(12) United States Patent
Gertsek et al.

(10) Patent No.: US 6,656,147 B1
(45) Date of Patent: Dec. 2, 2003

(54) METHOD AND DELIVERY DEVICE FOR THE TRANSDERMAL ADMINISTRATION OF A SUBSTANCE

(75) Inventors: Marina Gertsek, Ridgewood, NJ (US); Bradley M. Wilkinson, North Haledon, NJ (US); Ronald J. Pettis, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 183 days.

(21) Appl. No.: 09/617,355

(22) Filed: Jul. 17, 2000

(51) Int. Cl.[7] .............................................. A61M 1/00
(52) U.S. Cl. ........................ 604/28; 604/27; 604/87; 604/185; 604/289; 604/290; 604/310
(58) Field of Search ................ 604/27, 3, 19, 604/290, 289, 87, 181, 182, 306, 310, 311, 185, 212, 218, 28

(56) References Cited

U.S. PATENT DOCUMENTS

| | | |
|---|---|---|
| 2,817,336 A | 12/1957 | Kravitz et al. |
| 4,330,220 A | 5/1982 | Schaar et al. |
| 5,250,023 A | 10/1993 | Lee et al. |
| 5,279,544 A * | 1/1994 | Gross et al. ................ 604/145 |
| 5,820,622 A * | 10/1998 | Gross et al. ................ 204/280 |
| 5,879,326 A | 3/1999 | Godshall et al. |
| 6,190,367 B1 * | 2/2001 | Hall ............................ 604/181 |

FOREIGN PATENT DOCUMENTS

| | | |
|---|---|---|
| FR | 2 581 569 | 11/1986 |
| GB | 2 221 394 A | 2/1990 |
| WO | WO97/03718 | 2/1997 |
| WO | WO 97/48440 | 12/1997 |

* cited by examiner

*Primary Examiner*—Timothy L. Maust
(74) *Attorney, Agent, or Firm*—Eric M. Lee

(57) ABSTRACT

A device for delivering a substance into the skin of a patient includes a housing and a plurality of microneedles for penetrating the skin. The housing includes a bottom wall with a plurality of apertures for supplying the substance to the microneedles. The housing also includes a flexible top cover member enclosing a bladder containing the substance to be delivered. The bottom wall of the housing has at least one cannula facing the bladder. Pressing on the top cover member causes the cannula to puncture the bladder and deliver the substance to the microneedles for delivery to the patient. In one embodiment, the cannula is surrounded by a flexible member to prevent piercing of the bladder until sufficient pressure is applied to the cover member to depress the flexible member.

57 Claims, 5 Drawing Sheets

METHOD AND DELIVERY DEVICE FOR THE TRANSDERMAL ADMINISTRATION OF A SUBSTANCE

FIELD OF THE INVENTION

The present invention relates to a method and delivery device for delivering a substance, such as a drug or pharmaceutical agent transdermally to a patient. More particularly, the invention is directed to a device containing a diluent for delivering a reconstituted drug transdermally to a patient.

BACKGROUND OF THE INVENTION

Various devices have been proposed for transdermally delivering pharmaceutical agents, drugs and other substances. Although the subcutaneous delivery methods using a standard cannula are effective for many applications, the pain normally induced by the cannula has prompted the development of less painful delivery methods.

The use of prefilled syringes and other delivery devices has increased significantly in recent years due in part to the convenience and reduced risk of contamination. Prefilled syringes are generally suitable for drug solutions that are stable for extended periods of time. The drug solution itself must be stable and the solution must not interact with the syringe barrel or other container during storage. Certain drugs are inherently unstable in solution and are normally stored as a dried or lyophilized powder that must be reconstituted prior to use. These drugs are not suitable for standard prefilled syringes.

A method that has received much attention in recent years is the delivery of drugs through the skin by forming micropores or cuts through the stratum corneum. By penetrating the stratum corneum and delivering the drug to the skin in or below the stratum corneum, many drugs can be effectively administered. The devices for penetrating the stratum corneum generally include a plurality of micron size needles or blades having a length to penetrate the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

The skin is made up of several layers with the upper composite layer being the epithelial layer. The outermost layer of the skin is the stratum corneum which has well known barrier properties to prevent molecules and various substances from entering the body and analytes from exiting the body. The stratum corneum is a complex structure of compacted keratinized cell remnants having a thickness of about 10–30 microns.

The natural impermeability of the stratum corneum prevents the administration of most pharmaceutical agents and other substances through the skin. Numerous methods and devices have been proposed to enhance the permeability of the skin and to increase the diffusion of various drugs through the skin so that the drugs can be utilized by the body. Typically, the delivery of drugs through the skin is enhanced by either increasing the permeability of the skin or increasing the force or energy used to direct the drug through the skin.

One example of a method for increasing the force for the delivery of drugs through the skin include iontophoresis. Iontophoresis generally applies an external electrical field to ionize the drug, thereby increasing the diffusion of the drug through the skin. However, it can be difficult to control the amount and rate of drug delivery using iontophoresis. Under some circumstances, iontophoresis can cause skin damage depending on the extent of ionization, the energy applied to ionize the drug and duration of the treatment.

Sonic, and particularly ultrasonic energy, has also been used to increase the diffusion of drugs through the skin. The sonic energy is typically generated by passing an electrical current through a piezoelectric crystal or other suitable electromechanical device. Although numerous efforts to enhance drug delivery using sonic energy have been proposed, the results generally show a low rate of drug delivery.

The prior methods and apparatus for the transdermal administration of drugs has exhibited limited success. Accordingly, a continuing need exists in the industry for an improved device for the administration of various drugs and other substances.

SUMMARY OF THE INVENTION

The present invention is directed to a method and device for the transdermal delivery of a substance, such as a drug, vaccine or other pharmaceutical agent, to a patient. In particular, the invention is directed to a method and device for delivering a pharmaceutical agent to the stratum corneum of the skin to a sufficient depth where the pharmaceutical agent can be absorbed and utilized by the body.

Accordingly, a primary object of the invention is to provide a method and device for reconstituting a pharmaceutical agent and administering the pharmaceutical agent transdermally through the skin substantially without pain to the patient.

Another object of the invention is to provide a prefilled delivery device having a reservoir containing a substance and a plurality of microneedles or blades for penetrating the stratum corneum of the skin for delivering the substance to the skin.

A further object of the invention is to provide a device having a dried pharmaceutical agent and a reservoir containing a diluent for reconstituting the dried pharmaceutical agent and delivering the pharmaceutical agent to the patient.

Another object of the invention is to provide a device having a bladder containing a substance and a cannula for piercing the bladder to dispense the substance and deliver the substance to the patient.

A further object of the invention is to provide a device for the transdermal delivery of a substance where the apparatus includes a bladder containing the substance, a cannula to pierce the bladder and a protecting shield to prevent premature piercing of the bladder.

A still further object of the invention is to provide a device for the transdermal delivery of a pharmaceutical agent having a plurality of microneedles for penetrating the stratum corneum and a bladder containing the pharmaceutical agent for delivering the pharmaceutical agent to the microneedles.

Another object of the invention is to provide a device having a plurality of microneedles for penetrating the stratum corneum and an outer adhesive patch for adhesively attaching the apparatus to the skin of a patient.

Still another object of the invention is to provide a transdermal delivery device having an array of microneedles for penetrating the stratum corneum of the skin, a flexible bladder containing a substance and flexible cover that can be deflected toward the bladder to dispense the substance to the microneedles.

A further object of the invention is to provide a device for the transdermal delivery of a substance to a patient where the device has an array of microneedles and a dried substance on the microneedles, where the dried substance is reconstituted by dispensing a diluent from a bladder within the device.

These and other objects of the invention are substantially attained by providing an intradermal delivery device for introducing a substance into the skin of a patient. The device comprises a housing having a central opening and a planar member positioned in the central opening of the housing. The planar member has an inner surface and an outer surface. The outer surface has a plurality of microneedles extending therefrom, at least one opening passing through the planar member from the inner surface to the outer surface, and at least one cannula on the inner surface. A flexible cover is coupled to the housing and overlies the central opening and is spaced from the planar member to define a cavity in the housing. A bladder containing at least one substance is positioned in the cavity of the housing between the planar member and the flexible cover. The bladder is piercable by the cannula and is collapsible by pressing the flexible cover to dispense the substance through the opening to the microneedles.

The objects and advantages of the invention are further attained by providing an intradermal device for administering a pharmaceutical agent through the skin of a patient. The device comprises a housing having a bottom wall and at least one side wall defining a cavity. The bottom wall has a plurality of microneedles and a plurality of passages extending through the bottom wall to the microneedles. A flexible cover is coupled to the housing and encloses the cavity. The flexible cover has a generally arcuate shaped outer surface in a first position and is movable from the first position to a second position toward the bottom wall. A bladder contains a substance and the bladder is positioned in the cavity and is collapsible by applying pressure to the flexible cover to dispense the substance through the passages in the bottom wall to the microneedles.

Another object of the invention is to provide a method of administering a substance such as a pharmaceutical agent through the skin of a patient which comprises providing a delivery device having a housing with a bottom wall and at least one side wall defining a cavity. The bottom wall has an outer surface with a plurality of microneedles extending therefrom and has a plurality of passages extending through the bottom wall from the cavity to the microneedles. A bladder contains at least one substance and is positioned in the cavity, and a flexible cover encloses the cavity. The device contacts the skin of a patient and sufficient pressure is applied to the device to cause the microneedles to penetrate the skin a sufficient depth for delivering a substance to the patient. Sufficient pressure is applied to the flexible cover to rupture the bladder and dispense the substance to the microneedles.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings in which.

DETAILED DESCRIPTION OF THE PREFERRED EMBODIMENTS

The present invention is directed to an intraepidermal delivery device for administering a substance to a patient. More particularly, the invention is directed to a prefilled delivery device containing a drug solution or diluent for a dried drug and to a method for administering the drug solution or a reconstituted drug solution into or below the stratum corneum of the skin of a patient. Intradermal refers to one or more layers within the skin and is not limited to the dermis layer of the skin.

The device and method of the present invention are particularly suitable for use in administering various substances, including pharmaceutical agents, to a patient, and particularly to a human patient. As used herein, a pharmaceutical agent includes a substance having biological activity that can be delivered through the body membranes and surfaces, and particularly the skin. Examples include various drugs, such as antibiotics, antiviral agents, analgesics, anesthetics, anorexics, antiarthritics, antidepressants, antihistamines, anti-inflammatory agents, antineoplastic agents, vaccines, including DNA vaccines, adjuvants, biologics, and the like. Other substances which can be delivered intradermally to a patient include proteins, peptides and fragments thereof. The proteins and peptides can be naturally occurring, synthesized or recombinantly produced.

The invention is directed to a delivery device 10 having a housing 12, a plurality of microneedles 14 and a prefilled bladder 16 as shown in FIGS. 1–4. The invention is further directed to a method of delivering a substance to a patient using the delivery device 10.

Figure 1:
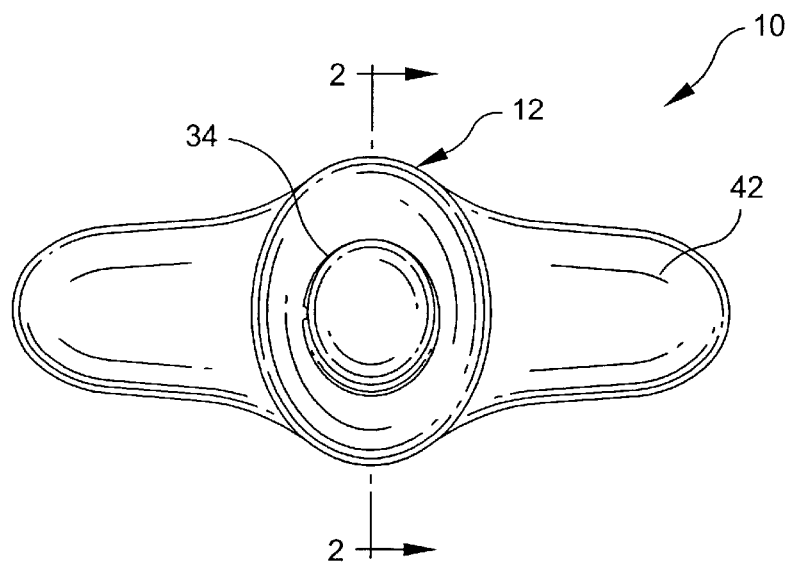
FIG. 1 is a top view of the transdermal delivery device in accordance with a first embodiment of the invention.
Figure 2:
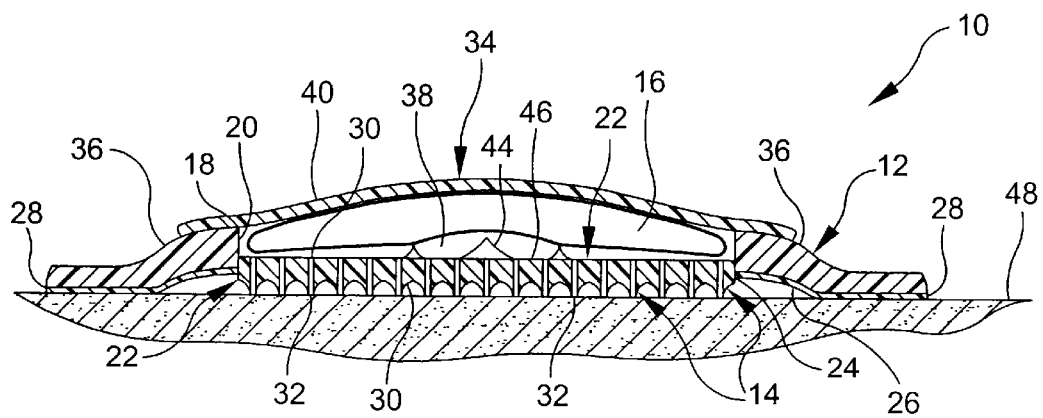
FIG. 2 is a cross-sectional view of the transdermal delivery device of FIG. 1.

Referring to FIGS. 1–4, the housing 12 of device 10 in this embodiment has a generally circular shape having a central opening 18 defining an inner wall 20. Housing 12 is preferably made of a flexible plastic or rubber-like material that is non-reactive to the substance being delivered to the patient. In the embodiment illustrated, the microneedles 14 are integrally formed with a planar member 22 that is dimensioned to fit within the central opening 18. Planar member 22 preferably has a shape corresponding to the shape of central opening 18 and fits securely against inner wall 20. An outer edge 24 of planar member 22 abuts inner wall 18 to form a fluid tight seal. In one embodiment of the invention, the planar member 22 is attached to the inner wall 20 by a suitable adhesive or other suitable bonding method. As shown in FIG. 2, planar member 22 is positioned in the central opening 18 of housing with the microneedles 14 facing outwardly beyond the housing 12 to ensure complete contact with the skin of the patient as discussed hereinafter in greater detail.

Housing 12 in the embodiment shown in FIGS. 1–4 is sufficiently flexible to conform to the contour of the patient's skin. In other embodiments, the housing can be made of a rigid material. A bottom surface 26 of housing 12 preferably includes a pressure sensitive adhesive 28 for attaching housing 12 to the skin of a patient during use. The pressure sensitive adhesive 28 can be a suitable adhesive as known in the art that is commonly used in adhesive bandages. The adhesive layer 28 preferably encircles the central opening 18 and is able to form a substantially fluid tight seal around the central opening 18 and microneedles 14.

Planar member 22 forms a bottom wall of housing 12 having the microneedles 14 facing outwardly from the housing 12. In the embodiment illustrated, microneedles 14 are integrally formed with the planar member 22. In alternative embodiments, a separate bottom wall can be provided and a second member having microneedles formed thereon can be superimposed.

As shown in FIG. 1, a flexible film 42 of a sheet material is attached to the housing 12. Film 42 has a dimension to extend beyond the dimension of the housing 12 in opposite directions. Film 42 includes an adhesive coating for attaching delivery device 10 to the skin of a patient in a manner similar to an adhesive bandage strip.

Delivery device 10 is generally made from a plastic material that is non-reactive with the substance being administered. Suitable plastic materials include, for example, polyethylene, polypropylene, polyesters, polyamides and polycarbonates as known in the art. The microneedles can be made from various materials by methods as known in the art. For example, microneedles can be made from silicon, stainless steel, tungsten steel, alloys of nickel, molybdenum, chromium, cobalt, and titanium, ceramics, glass polymers and other non-reactive metals, and alloys thereof.

The length and thickness of the microneedles are selected based on the particular substance being administered and the thickness of the stratum corneum in the location where the device is to be applied. In one embodiment, the microneedles penetrate the stratum corneum substantially without penetrating or passing through the epidermis. The microneedles can have a length for penetrating the skin up to about 250 microns. Suitable microneedles have a length of about 5 to 200 microns. Typically, the microneedles have a length of about 5 to about 100 microns, and generally in the range of about 10 to 40 microns. The microneedles in the illustrated embodiment have a generally conical shape. In alternative embodiments, the microneedles can be triangles, flat blades or pyramids. Typically, the microneedles are perpendicular to the plane of the device. The width of the microneedles can be about 15 to 40 gauge to obtain optimum penetration of the skin.

The microneedles 14 are generally formed in uniformly spaced rows and columns to form an array. The microneedle array generally has a surface area of about 0.5 to about 5.0 $cm^2$. The spacing between the rows and columns can be varied depending on the substance being administered and the desired dosage. In one embodiment, the microneedles are spaced apart a distance of about 0.05 mm to about 5.0 mm.

In the embodiment of FIGS. 1–4, microneedles 14 include a hollow passage 30 extending axially through each microneedle 14 and planar member 22. Passage 30 of each microneedle is dimensioned to allow fluid to pass through the microneedles to the tips 32 of the microneedles for delivery to the skin surface.

A generally domed shaped cover member 34 is attached to a top surface 36 of housing 12 to completely cover central opening 18 and define a cavity 38 within housing 12. As shown in FIG. 2, cover member 34 has a dimension slightly larger than the dimension of central opening 18 and has a generally convex outer surface 40. Cover member 34 is preferably made of a plastic sheet material that is sufficiently flexible to be flexed in a generally downward direction. In one embodiment, cover member 34 is made of material that has sufficient memory to return to its domed shape and can be depressed to snap to an inverted concave shape.

Flexible bladder 16 is positioned in cavity 38 of housing 12. Bladder 16 is preferably a sealed bulbous shaped member made from a flexible material that can conform to the shape of cavity 38 and can be depressed to dispense the contents. Bladder 16 is prefilled with a desired substance before the delivery device is assembled.

A cannula 44 is provided on the top surface 46 of planar member 22 as shown in FIG. 2. In the embodiment illustrated, three cannulas 44 are positioned to face toward bladder 42, although the number used can vary as needed. Cannula 44 has a generally flat base 46 and a pointed tip 48 that is capable of piercing the bladder. Cannula 44 can be made of suitable metal or plastic having sufficient strength to pierce bladder 42. As shown in FIG. 2, cannula 44 is a separate element that is attached to planar member 22. In alternative embodiments, cannula 44 can be integrally formed with planar member 22. Typically, cannula 44 has a generally conical shape, although can be any suitable shape capable of piercing bladder 16.

Bladder 16 can contain a drug solution or other substance to be delivered to the patient. Preferably, bladder 16 is dimensioned to contain a premeasured dosage for the particular drug solution being administered.

In further embodiments, bladder 16 contains a diluent or carrier for reconstituting a substance to be delivered to the patient. The diluent can be, for example, distilled water or saline solution. In a preferred embodiment, a dried drug is provided as a coating on the outer surfaces of the microneedles. In further embodiments, the dried drug can be a coating on the top surface of planar member 22 or in passages 30. In this embodiment, the dried or lyophilized drug or pharmaceutical agent is dissolved or dispersed in the diluent and delivered to the patient. This embodiment is particularly suitable for unstable drug solutions.

Delivery device 10 is produced as a complete, prefilled unit for delivery of a substance to a patient. The device can include a protective cover (not shown) over microneedles 14 to prevent damaging or contamination of the microneedles during storage and shipping. Similarly, a protective release liner (not shown) can be applied over the adhesive and the device packaged in a suitable packaging material commonly used for medical devices.

The primary barrier properties of the skin including the resistance to drug penetration reside in the outermost layer of the skin, referred to as the stratum corneum. The inner layers of the epidermis generally include three layers, commonly identified as the stratum granulosum, the stratum malpighii, and the stratum germinativum. Once a drug or other substance penetrates below the stratum corneum, there is substantially less resistance to permeation into the subsequent layers of the skin and eventual absorption by the body. Thus, delivery of a substance below the stratum corneum can be an effective system for administering some substances, and particularly some vaccines, to the body. The delivery device of the invention is able to deliver a substance into or below the stratum corneum where it can be utilized by the body. Preferably, the device and method of the invention pierce the stratum corneum substantially without penetrating the dermis to target the tissue layers below the stratum corneum. As used herein, the term penetrate refers to entering a layer of the skin without necessarily passing completely through. Piercing refers to passing completely through a layer of the skin. As used herein, transdermal refers to the delivery of a substance, such as a pharmaceutical, biological agent or vaccine, through one or more layers of skin.

Figure 3:
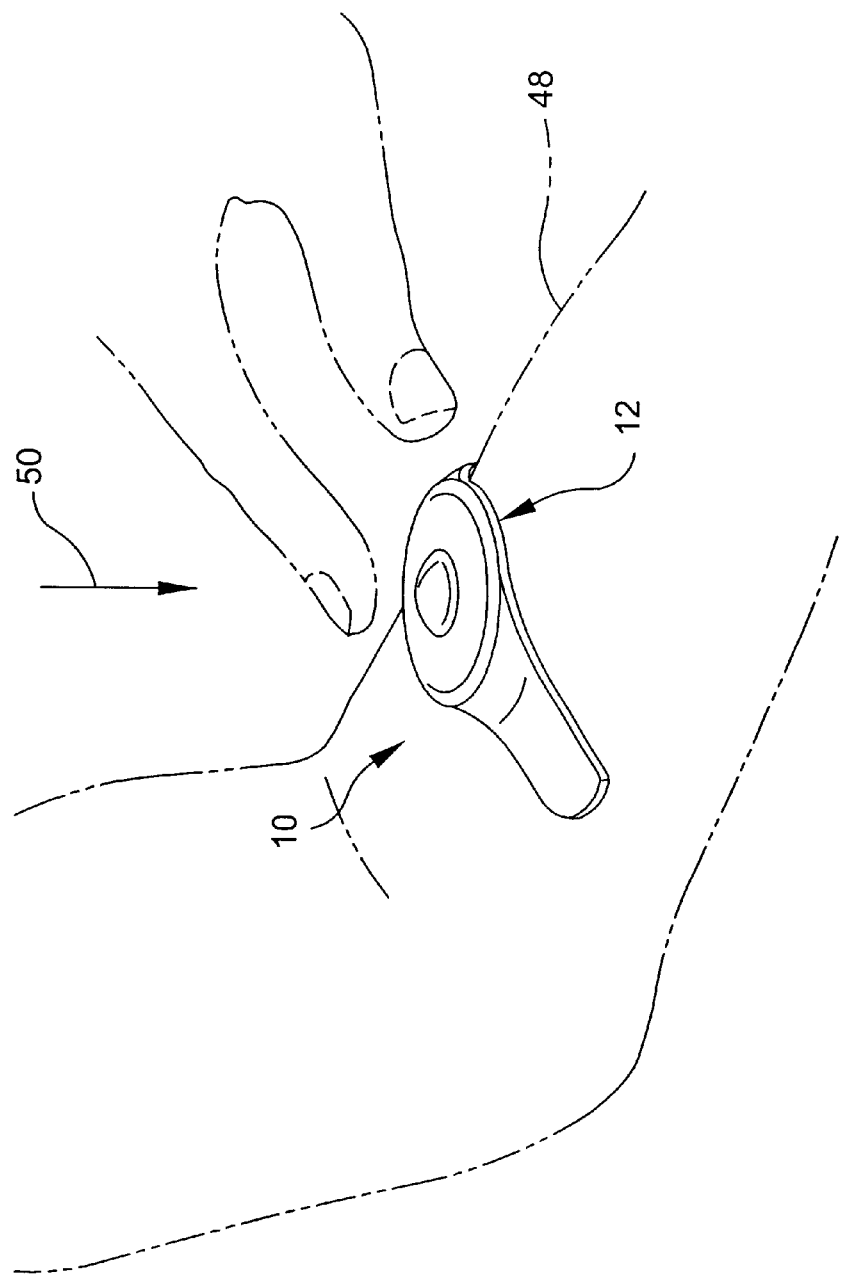
FIG. 3 is a perspective view of the transdermal delivery device of FIG. 1.
Figure 4:
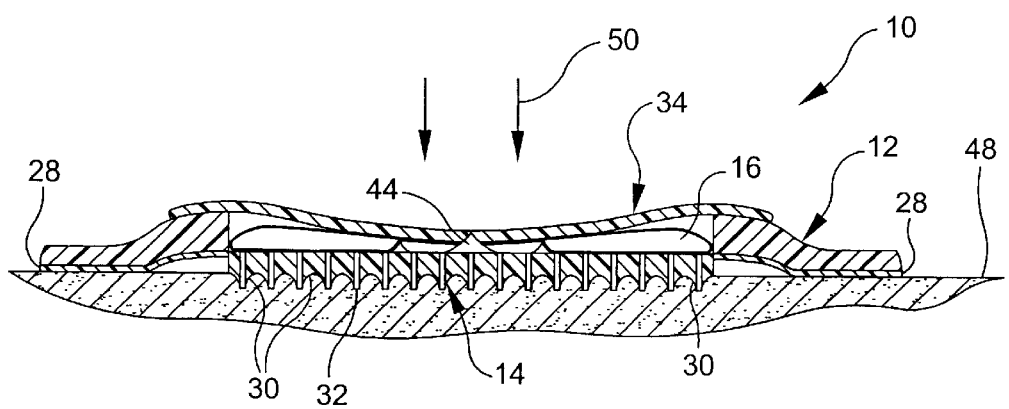
FIG. 4 is a side view in cross-section of a transdermal delivery device of FIG. 1 showing the outer cover and bladder depressed.

In use, delivery device 10 is removed from its packaging and the release sheet, if provided, is separated to expose the adhesive layer on the bottom face of the device. Delivery device 10 is positioned on the desired location of the skin 48 and pressed in place with a gentle downward pressure until the microneedles penetrate the outermost layer of skin and the adhesive layer contacts the skin and forms a seal around the microneedle array. A gentle rubbing motion also can be applied to delivery device 10 to assist in the penetration of the skin by the microneedles 14. Cover member 34 is then pushed downwardly in the direction of arrow 50 as shown in FIGS. 3 and 4 with sufficient pressure to cause cannula 44 to pierce bladder 16. The pressure is applied to cover member 34 and bladder 16 to collapse the bladder and force the contents of the bladder into cavity 38 and through passages 30 to tips 32 of the microneedles 14. Preferably, adhesive layer 28 on the bottom of housing 12 and film 42 form a seal to contain the drug solution or other substance in the target area of the microneedle array where it can penetrate the stratum corneum and be absorbed by the body.

Generally, the pressure applied to cover 34 is sufficient to enable a drug solution to flow to the tips of the microneedles 14 where the drug solution is available for absorption by the skin. In further embodiments, cover member 34 can be made of stiff plastic material so that when pressed, the dome shaped cover member snaps to an inverted position and retains the inverted position to maintain a constant force on the bladder. In this manner, a constant pressure can be produced to deliver the substance to the microneedles.

Figure 5:
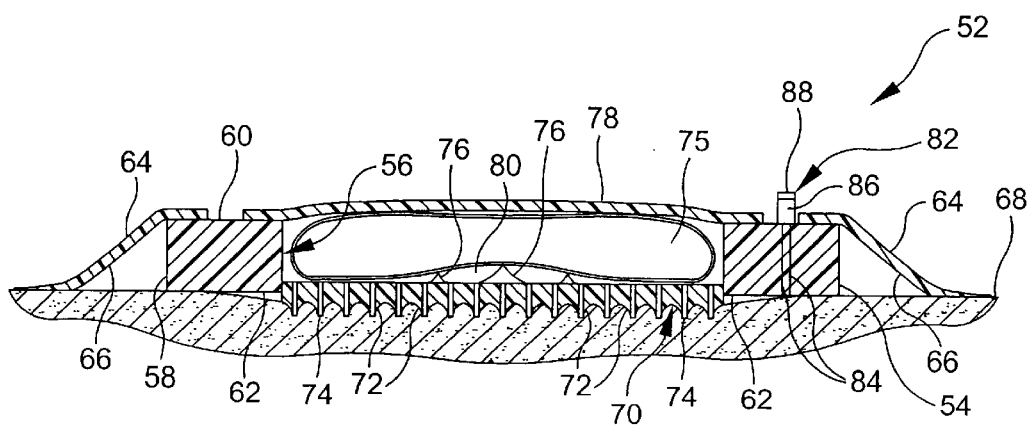
FIG. 5 is a side elevational view in cross-section of a second embodiment of the invention.

Embodiment of FIG. 5

FIG. 5 shows a second embodiment of the delivery device 52. Delivery device 52 is similar to the embodiment of FIGS. 1–4 and includes a housing 54 having a central opening 56, a bottom surface 58 and a top surface 60. Bottom surface 58 is preferably provided with a layer of a pressure sensitive adhesive 62 that encircles central opening 56. A flexible film 64 having an adhesive 66 is attached to top surface 60 of housing 54 for attaching delivery device 52 to the skin 68 of a patient.

A planar member 70 is formed with an array of microneedles 72. Microneedles 72 are provided with an axial hollow passage 74 extending through planar member 70. A bladder 75 contains a drug solution, diluent or other substance as in the previous embodiment. A cannula 76 is provided on the top surface of planar member 70, and a flexible cover 78 is attached to housing 54 to enclose a cavity 80.

In the embodiment of FIG. 5, an indicator device 82 is provided in housing 54 for indicating proper contact of the microneedle array with skin 68 of the patient. In the embodiment illustrated, indicator device 82 is an electrical device that contacts the skin when sufficient downward pressure is applied to delivery device 52. Indicator device 82 includes a pair of electrodes 84 connected by leads extending from the bottom surface 62 of housing 54 to top surface 60. Electrodes 84 are coupled to a power source 86 having a visual indicator 88, such as, for example, a liquid crystal display or liquid crystal diode.

Delivery device 54 is applied to skin 68 of a patient with a downward pressure until electrodes 84 contact skin 68. The conductivity of the patient's skin completes the electrical circuit between electrodes 84 to actuate indicator 88 thereby providing an indication that sufficient pressure is applied for microneedles 72 to penetrate the skin a sufficient depth for delivery of the drug solution. Cover member 78 is then depressed to pierce bladder 75 by cannula 76 and dispense the contents of bladder 75.

In the embodiment illustrated, the indicator device is an electrical device that relies on the electrical conductivity of the skin of the patient. In further embodiments, the indicator can be a pressure sensor device or other suitable devices capable of providing an indication that sufficient pressure is applied to the microneedle array.

Figure 6:
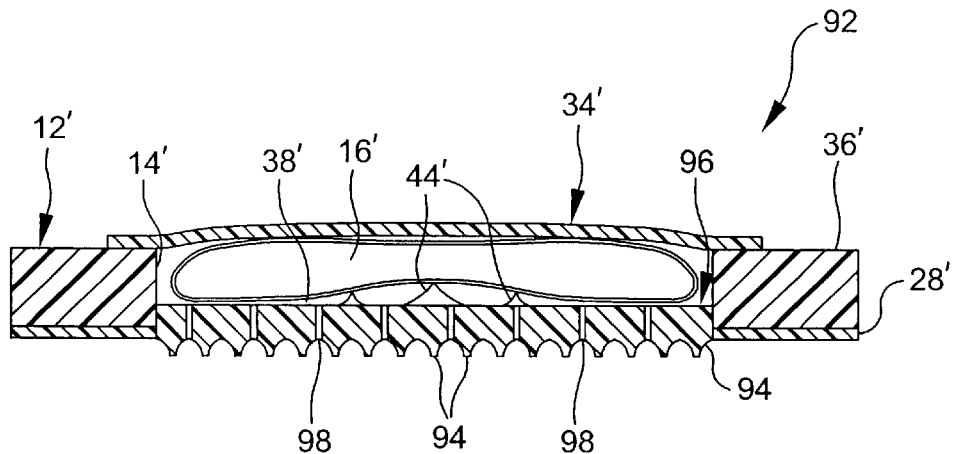
FIG. 6 is side elevational view in cross-section of the delivery device in a third embodiment of the invention.

Embodiment of FIG. 6

FIG. 6 shows a delivery device 92 in a further embodiment of the invention. Delivery device 92 is similar to the delivery device 10 of FIGS. 1–4 except for the array of microneedles 94. Accordingly, identical components are identified by the same reference number with the addition of a prime.

The microneedle array 94 is formed on a bottom surface of a planar member 96. As in the previous embodiments, the planar member 96 is coupled to housing 12' in the central opening 14' to define a cavity. A plurality of passages 98 extend through the planar member 96 from the cavity to the outer face. In this embodiment, microneedles 94 are solid structures and passages 98 terminate substantially at the base of the microneedles and between adjacent microneedles 94.

Delivery device 92 is used in substantially the same manner of the previous embodiments. Delivery device 92 is positioned on the skin and rubbed or pressed gently to enable microneedles 94 to penetrate the skin. Cover member 34' is then pressed to cause bladder 16' to be pierced by cannula 44'. The substance contained in the bladder 16' is then dispensed and directed to passages 98 to microneedles 94. As in the previous embodiments, bladder 16' can contain a drug solution or a diluent to dissolve a dried drug in the cavity 38' or on the surface of the microneedles 94.

Figure 7:
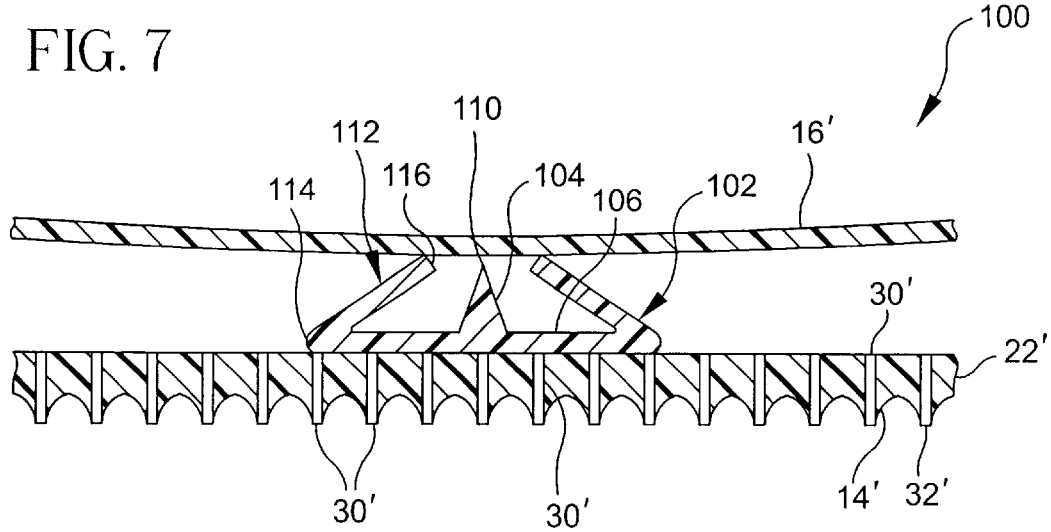
FIG. 7 is a partial side view of the transdermal delivery device in a fourth embodiment of the invention.
Figure 8:
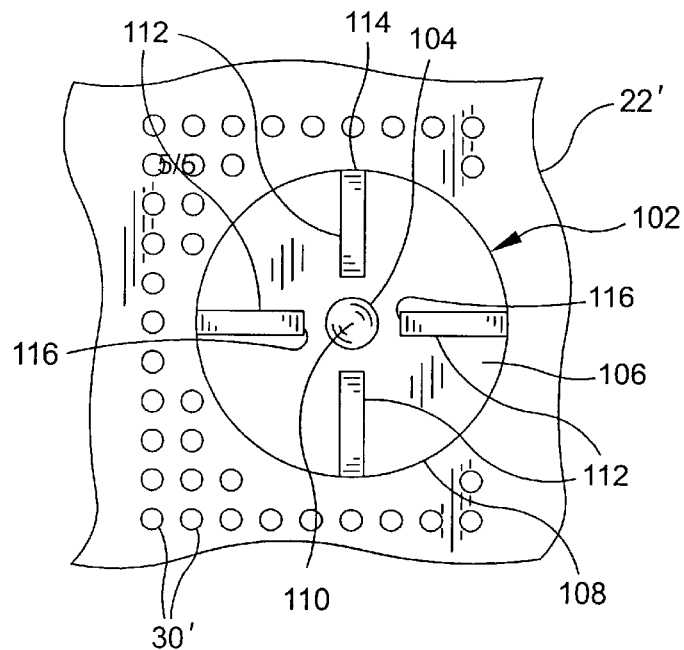
FIG. 8 is a partial top view of the embodiment of FIG. 7.
Figure 9:
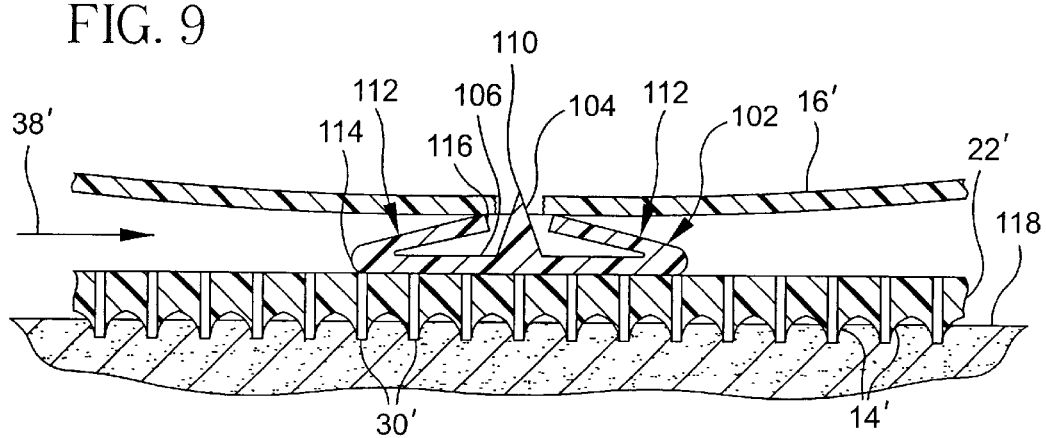
FIG. 9 is a partial cross-sectional side view of the embodiment of FIG. 7 showing the bladder pierced by the cannula.

Embodiment of FIGS. 7–9

A delivery device 100 in a further embodiment is shown in FIGS. 7–9. Delivery device 100 is similar to delivery device 10 of the embodiment of FIGS. 1–4, except for a protecting shield device 102 that cooperates with a cannula 104. Accordingly, identical components are identified by the same reference number with the addition of a prime.

As in the previous embodiment, delivery device 100 includes a planar member 22' having an array of microneedles 14' on a bottom surface of the planar member 22'. Microneedles 14' include an axial passage 30' that extends through planar member 22' to cavity 38'.

The protecting member 102 is a supporting or cradle-like device that is positioned in the upper surface of planar member 22' to shield cannula 104 for preventing or resisting premature rupturing and piercing of bladder 16'. As shown in FIGS. 6 and 7, protecting member 100 includes a base 106 having an outer edge 108 and has a height greater than a height of cannula 104. In the embodiment illustrated, base 106 is a flat circular member, although the actual shape of the base can be varied depending on the particular needs of the device.

A cannula 104 is coupled to base 106 and extends in a generally upward direction away from planar member 22' toward bladder 16'. Cannula 104 in the embodiment illustrated is a separate member coupled to base 106 by a suitable adhesive, welding or the like. In alternative embodiments, cannula 104 can be integrally formed with the base. Cannula 104 has a generally conical shape converging to a sharp tip 110 suitable for piercing bladder 16'.

A resilient arm 112 has a first end 114 coupled to the base 106 and a second end 116 extending away from the base 106. In the embodiment of FIGS. 7–9, four arms 112 are coupled to the base 106 and extend at an incline toward the tip 110 of cannula 104. The arms 112 are positioned such that the second free ends 116 of arms 112 assume a normal position above tip 110 of cannula 108 as shown in FIG. 7. Arms 112 surround tip 110 of cannula 104 and support bladder 16' above cannula 104 to prevent bladder 16' from contacting cannula 104 during shipping and storage. In the embodiment illustrated, arms 112 are integrally formed with base 106, although in other embodiments, the arms 112 can be separate members that are assembled together.

The delivery device 100 is used in a manner similar to the previous embodiments. Delivery device 100 is positioned on the skin 118 of the patient and gently rubbed and pressed against skin 118 and secured in place by the adhesive. Cover member 34' is then pushed downwardly to push bladder 16' toward cannula 104. Arms 112 of protecting member 102 are sufficiently flexible that downward pressure on cover member 34' and bladder 16' pivots free end 116 of arms 112 toward base 106 to enable cannula 104 to pierce bladder 16' as shown in FIG. 9 to dispense the contents of the bladder.

The delivery devices of the invention are generally intended for single use and contain a selected dose for the substance being delivered to the patient. The adhesive film is able to hold the delivery device in place with minimal discomfort for extended periods of time. The length of time the delivery device remains in contact with the skin can vary from several minutes to several hours. Various factors that determine the length of time the delivery device remains in contact with the skin include, for example, the depth of penetration, the volume of the substance being delivered, and the absorption rate of the substance.

While several embodiments have been shown to illustrate the present invention, it will be understood by those skilled in the art that various changes and modifications can be made therein without departing from the scope of the invention as defined in the appended claims.

What is claimed is:

1. A device for introducing a substance into the skin of a patient, said device comprising:
   a housing having a central opening;
   a planar member positioned in said central opening of said housing, said planar member having an inner surface and an outer surface, said outer surface having a plurality of microneedles extending therefrom, at least one opening passing through said planar member from said inner surface to said outer surface, and at least one cannula on said inner surface;
   a flexible, deformable cover coupled to said housing and overlying said central opening and being spaced from said planar member to define a cavity in said housing; and
   a bladder containing at least one substance and being positioned in said cavity of said housing between said planar member and said flexible cover, said bladder being piercable by said cannula and collapsible by pressing and deforming said flexible cover to dispense said substance through said opening to said microneedles.

2. The device of claim 1, further comprising a dry pharmaceutical agent, wherein said substance contained in said bladder is a diluent.

3. The device of claim 2, wherein said dry pharmaceutical agent is provided in said at least one opening in said planar member.

4. The device of claim 2, wherein said dry pharmaceutical agent is provided on said microneedles.

5. The device of claim 2, wherein said dry pharmaceutical is provided on said inner surface of said planar member.

6. The device of claim 1, wherein said dry pharmaceutical agent is provided in said cavity.

7. The device of claim 1, wherein said cannula is a substantially conical shaped member having a tip facing said bladder.

8. The device of claim 1, wherein said cannula is integrally formed on said inner surface of said planar member.

9. The device of claim 1, wherein said microneedles have a length for penetrating the stratum corneum of the skin.

10. The device of claim 1, comprising a plurality of said openings in said planar member, said openings extending through a respective microneedle.

11. The device of claim 1, wherein said at least one opening in said planar member is adjacent at least one of said microneedles.

12. The device of claim 1, wherein said flexible cover is made of a resilient material and movable from a first position having a generally convex outer surface to a second position having a generally concave outer surface.

13. The device of claim 12, wherein said flexible cover is made from a stiff plastic material having a memory and is able to snap from said first position to said second position.

14. The device of claim 1, wherein said microneedles have a length of about 10 to 40 microns.

15. A device for introducing a substance into the skin of a patient, said device comprising:
    a housing having a central opening;
    a bottom member positioned in said central opening of said housing, said member having an inner surface and an outer surface, said outer surface having a plurality of microneedles extending therefrom, at least one opening passing through said member from said inner surface to said outer surface, and at least one cannula;
    a flexible cover coupled to said housing and overlying said central opening and being spaced from said member to define a cavity in said housing, wherein said housing has a bottom surface surrounding said member, said device further comprising an adhesive on said bottom surface for attaching said housing to the skin of a patient; and
    a bladder containing at least one substance and being positioned in said cavity of said housing between said member and said flexible cover, said bladder being piercable by said cannula and collapsible by pressing said flexible cover to dispense said substance through said opening to said microneedles.

16. The device of claim 1, further comprising a flexible film having a bottom face attached to said housing, said flexible film surrounding said housing and extending outwardly therefrom, and an adhesive on said bottom face for attaching said device to the skin of a patient.

17. The device of claim 1, further comprising a protecting member on said inner surface of said bottom wall, said protecting member having a height greater than a height of said cannula and being positioned to prevent said bladder from contacting said cannula until sufficient pressure is applied to said flexible cover.

18. The device of claim 17, wherein said protecting member includes a base coupled to said inner surface of said bottom wall, and having at least one flexible arm coupled to said base and extending in a direction toward said bladder, said at least one arm having a length to prevent said bladder from contacting said cannula and being sufficiently flexible, wherein a force applied to said flexible cover flexes said arm toward said bottom wall whereby said bladder contacts said cannula.

19. The device of claim 1, wherein said housing includes an indicating device for indicating contact of said device with the skin of a patient.

20. The device of claim 19, wherein said indicating device includes a pair of electrodes for contacting the skin, a power source coupled to said electrodes and an indicator coupled to said power source and said electrodes.

21. A delivery device for delivering a substance to the skin of a patient, said device comprising:
a housing having a bottom wall and at least one side wall defining a cavity, said bottom wall having a plurality of microneedles and a plurality of passages extending through said bottom wall to said microneedles;
a flexible cover coupled to said housing and enclosing said cavity, said flexible cover having a generally arcuate shaped outer surface in a first position and being deformable from said first position to a second position toward said bottom wall; and
a bladder containing a substance, said bladder being positioned in said cavity and being collapsible by applying pressure to said flexible cover to dispense said substance through said passages in said bottom wall to said microneedles.

22. The delivery device of claim 21, wherein said substance contained in said bladder is a diluent and said cavity contains at least one dried pharmaceutical agent that is soluble or dispersible in said diluent.

23. The delivery device of claim 21, wherein said substance contained in said bladder is a diluent and said microneedles include a coating of at least one dried pharmaceutical agent that is soluble or dispersible in said diluent.

24. The delivery device of claim 21, further comprising a cannula in said cavity and being positioned to pierce said bladder by applying sufficient force to said flexible cover.

25. The delivery device of claim 24, wherein said cannula is positioned on said bottom wall of said housing.

26. The delivery device of claim 21, wherein said microneedles are hollow to form a passage from said cavity to a tip of said microneedles.

27. A delivery device for delivering a substance to the skin of a patient, said device comprising:
a housing having a bottom wall and at least one side wall defining a cavity, said bottom wall having a plurality of microneedles and a plurality of passages extending through said bottom wall to said microneedles;
a flexible cover coupled to said housing and enclosing said cavity, said flexible cover having a generally arcuate shaped outer surface in a first position and being movable from said first position to a second position toward said bottom wall;
a bladder containing a substance, said bladder being positioned in said cavity and being collapsible by applying pressure to said flexible cover to dispense said substance through said passages in said bottom wall to said microneedles; and
a flexible film attached to said housing, said film surrounding said housing and extending outwardly therefrom, and having an adhesive on a bottom face for attaching said delivery device to the skin of a patient.

28. The delivery device of claim 24, further comprising a protecting member on an inner surface of said bottom wall, said protecting member having a height greater than a height of said cannula and being positioned to prevent said bladder from contacting said cannula until sufficient pressure is applied to said flexible cover.

29. The delivery device of claim 28, wherein said protecting member includes a base coupled to said inner surface of said bottom wall, and having at least one flexible arm coupled to said base and extending in a direction toward said bladder, said flexible arm being sufficiently flexible to bend toward said bottom wall by applying sufficient pressure to said cover member, whereby said cannula pierces said bladder.

30. A method of administering a substance through the skin of a patient, comprising the steps of
providing a delivery device having a housing with a bottom wall and at least one side wall defining a cavity, said bottom wall having an outer surface with a plurality of microneedles extending therefrom and having a plurality of passages extending through said bottom wall from said cavity to said microneedles, a bladder containing at least one substance and being positioned in said cavity, and a flexible, deformable cover enclosing said cavity;
contacting said device to the skin of a patient and applying sufficient pressure to said device to cause said microneedles to penetrate the skin a sufficient depth for delivering said substance to the patient; and
applying sufficient pressure to said flexible cover to rupture said bladder and dispense said substance to said microneedles.

31. The method of claim 30, wherein said device includes a dry pharmaceutical agent and said substance contained in said bladder is a diluent.

32. The method of claim 30, wherein said dry pharmaceutical agent is provided in said cavity.

33. The method of claim 30, wherein said device includes a cannula positioned in said cavity and having a tip positioned for piercing said bladder, said method comprising applying sufficient pressure to said cover to cause said cannula to pierce said bladder.

34. The method of claim 33, wherein said cannula is integrally formed on an inner surface of said bottom wall.

35. The method of claim 30, wherein said passages in said bottom wall are adjacent said microneedles.

36. The method of claim 30, wherein said flexible cover is made of a resilient material and movable from a first position having a generally convex outer surface to a second position having a generally concave outer surface.

37. The method of claim 30, said device further comprising a flexible film having a bottom face attached to said housing, said flexible film surrounding said housing and extending outwardly therefrom, and an adhesive on said bottom face, said method comprising pressing said flexible film to attach said device to the skin of a patient.

38. A method of administering a substance through the skin of a patient, comprising the steps of
providing a delivery device having a housing with a bottom wall and at least one side wall defining a cavity, said bottom wall having an outer surface with a plurality of microneedles extending therefrom and having a plurality of passages extending through said bottom wall from said cavity to said microneedles, a bladder containing at least one substance and being positioned in said cavity, and a flexible, deformable cover enclosing said cavity;

said device further comprising a resilient protecting member on said inner surface of said bottom wall, said protecting member having a height greater than a height of said cannula and being positioned to prevent said bladder from contacting said cannula, said method comprising pressing said cover with sufficient pressure to push said bladder into contact with said cannula to pierce said bladder;

contacting said device to the skin of a patient and applying sufficient pressure to said device to cause said microneedles to penetrate the skin a sufficient depth for delivering said substance to the patient; and applying sufficient pressure to said flexible cover to rupture said bladder and dispense said substance to said microneedles.

39. The method of claim 38, wherein said protecting member includes a base coupled to said inner surface of said bottom wall, and having at least one flexible arm coupled to said base and extending in a direction toward said bladder, said at least one arm having a length to prevent said bladder from contacting said cannula, said method comprising applying sufficient pressure to said cover to flex said arm toward said bottom wall whereby said bladder is pierced by said cannula.

40. A device for introducing a substance into the skin of a patient, said device comprising:
 a housing having a central opening;
 a bottom member positioned in said central opening of said housing, said member having an inner surface and an outer surface, said outer surface having a plurality of microneedles extending therefrom, at least one opening passing through said member from said inner surface to said outer surface;
 a flexible cover coupled to said housing and overlying said central opening and being spaced from said member to define a cavity in said housing;
 a cannula extending into said central opening;
 a bladder containing at least one substance and being positioned in said cavity of said housing between said member and said flexible cover, said bladder being piercable by said cannula and collapsible by pressing said flexible cover to dispense said substance through said opening to said microneedles; and
 a protecting member in said cavity to prevent said bladder from contacting said cannula until sufficient pressure is applied to said flexible cover.

41. The device of claim 40, wherein said protecting member surrounds said cannula.

42. The device of claim 40, wherein said cannula is on said inner surface of said bottom member.

43. The device of claim 42, wherein said protecting member is on said inner surface of said bottom member.

44. The device of claim 40, wherein said protecting member has a height greater than a height of said cannula.

45. The device of claim 44, wherein said protecting member is a flexible member and deforms when a sufficient pressure is applied to said cover.

46. The device of claim 44, wherein said protecting member includes a flexible arm, said arm being sufficiently flexible to bend toward said bottom wall by applying sufficient pressure to said cover member.

47. The device of claim 40, wherein said protecting member includes a base and at least one flexible arm coupled to said base and extending in a direction toward said bladder a distance to prevent said bladder from contacting said cannula.

48. The device of claim 47, wherein said at least one flexible arm is sufficiently flexible to bend toward said base by applying sufficient pressure to said bladder.

49. A delivery device for delivering a substance to the skin of a patient, said device comprising:
 a housing having a bottom wall and at least one side wall defining a cavity, said bottom wall having a plurality of microneedles and a plurality of passages extending through said bottom wall to said microneedles;
 a flexible cover having an outer portion coupled to said housing and a central portion enclosing said cavity, said outer portion of said flexible cover being deformable from a first position spaced from said bottom wall to a second position toward said bottom wall; and
 a bladder containing a substance, said bladder being positioned in said cavity and being collapsible by applying pressure to said flexible cover to dispense said substance through said passages in said bottom wall to said microneedles.

50. The delivery device of claim 49, wherein said bottom wall has an outer edge surrounding said microneedles and an adhesive on said outer edge for attaching said housing to the skin of a patient.

51. The delivery device of claim 49, further comprising a flexible film attached to said housing and extending outwardly therefrom, and an adhesive on a bottom face of said flexible film for attaching said device to the skin of a patient.

52. The delivery device of claim 49, further comprising a cannula positioned in said cavity for piercing said bladder and a protecting member positioned in said cavity to prevent said cannula from piercing said bladder until sufficient pressure is applied to said bladder.

53. The delivery device of claim 52, wherein said protecting member includes at least one flexible arm.

54. A delivery device for delivering a substance to the skin of a patient, said device comprising:
 a housing having a bottom wall and at least one side wall defining a cavity, said bottom wall having a plurality of microneedles and a plurality of passages extending through said bottom wall to said microneedles and a cannula extending into said cavity;
 a bladder containing a substance, said bladder being positioned in said cavity and being collapsible by applying pressure to said bladder toward said bottom wall to dispense said substance through said passages in said bottom wall to said microneedles; and
 a protecting member positioned in said cavity to prevent said bladder from contacting said cannula until sufficient pressure is applied to said bladder.

55. The delivery device of claim 53, wherein said protecting member surrounds said cannula.

56. The delivery device of claim 54, wherein said protecting member has a height greater than a height of said cannula.

57. The delivery device of claim 56, wherein said protecting member has at least one flexible arm extending in a direction toward said bladder.

* * * * *